United States Patent
Satomi et al.

(10) Patent No.: US 7,196,232 B2
(45) Date of Patent: Mar. 27, 2007

(54) 4,4'-DIHYDROXYPHENYL BICYCLOHEXENES

(75) Inventors: Kouji Satomi, Wakayama (JP); Hiroyasu Oono, Wakayama (JP); Kenji Ekawa, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 56 days.

(21) Appl. No.: 10/531,358

(22) PCT Filed: Oct. 16, 2003

(86) PCT No.: PCT/JP03/13222

§ 371 (c)(1),
(2), (4) Date: Sep. 29, 2005

(87) PCT Pub. No.: WO2004/035513

PCT Pub. Date: Apr. 29, 2004

(65) Prior Publication Data

US 2006/0129001 A1    Jun. 15, 2006

(30) Foreign Application Priority Data

Oct. 17, 2002    (JP) .............................. 2002-302887

(51) Int. Cl.
C07C 39/12    (2006.01)
(52) U.S. Cl. ...................................... 568/719
(58) Field of Classification Search ................. 568/719
See application file for complete search history.

(56) References Cited

FOREIGN PATENT DOCUMENTS

| JP | 01-299821 | 12/1989 |
|----|-----------|---------|
| JP | 02-311524 | 12/1990 |
| JP | 07-278249 | 10/1995 |
| JP | 2000-034248 | 2/2000 |

OTHER PUBLICATIONS

Journal of Chemical Research, Synopses (1996), (7), 318-319.*

* cited by examiner

*Primary Examiner*—Thurman K. Page
*Assistant Examiner*—Kellette Gale
(74) *Attorney, Agent, or Firm*—Knobbe, Martens, Olson & Bear LLP

(57) ABSTRACT

Produce new 4,4'-dihydroxyphenyl bicyclohexenes that are useful as a material for liquid crystal polyester, polycarbonate, polyurethane or other synthetic resins or for photoresist used with display elements, semiconductors, etc., by thermally decomposing 4,4,4'4'-tetrahydroxyphenyl bicyclohexanes, preferably in the presence of alkali catalyst.

20 Claims, No Drawings

4,4'-DIHYDROXYPHENYL BICYCLOHEXENES

This application is the U.S. National Phase under 35 U.S.C. §371 of International Application PCT/JP2003/013222, filed Oct. 16, 2003, which claims priority to Japanese Patent Application No. 2002-302887, filed Oct. 17, 2002. The International Application was not published under PCT Article 21(2) in English.

TECHNICAL FIELD

This invention relates to new 4,4'-dihydroxyphenyl bicyclohexenes that have no substitutional group in either of the hydroxyphenyl groups or have a lower alkyl group in both hydroxyphenyl groups.

BACKGROUND TECHNOLOGY

Several 1,4'-hydroxyphenyl-substituted cyclohexenes are disclosed by the Chemical Abstracts Service, such as one in which the carboxymethyl group and naphthyl group are substituted (CAS Registration No. 101789-46-2) and one in which the phenyl group is substituted (CAS Registration No. 202266-25-9).

However, no 4,4'-hydroxyphenyl-substituted bicyclohexenes have been known that have a bicyclohexene structure.

These 4,4'-hydroxyphenyl-substituted bicyclohexenes are expected to offer improved performance compared with compounds having the aforementioned cyclohexene structure in terms of melting point, heat resistance and weather resistance, among others, and the 4,4'-hydroxyphenyl-substituted bicyclohexenes themselves are useful as a material for liquid crystal polyester, polycarbonate, polyurethane or other synthetic resins or for photoresist used with display elements, semiconductors, etc.

In addition, 4,4'-hydroxyphenyl-substituted bicyclohexenes also provide utility as an intermediate in various useful compounds. For example, by dehydrogenating the cyclohexene part of 4,4'-hydroxyphenyl-substituted bicyclohexenes, 4,4'-hydroxyphenyl-substituted biphenyls can be produced. Alternatively, by hydrogenating the cyclohexene part of 4,4'-hydroxyphenyl-substituted bicyclohexenes, 4,4'-hydroxyphenyl-substituted bicyclohexanes can be produced. The obtained compounds are also expected to be useful as a material for liquid crystal polyester, polycarbonate, polyurethane or other synthetic resins or for photoresist used with display elements, semiconductors, etc.

Patent Literature
Publication of Unexamined Patent Application No. 2000-34248
Non-Patent Literature
CAS Registration No. 101789-46-2
CAS Registration No. 202266-25-9

SUMMARY OF THE INVENTION

The present invention provides new 4,4'-dihydroxyphenyl bicyclohexenes that have no substitutional group in either of the hydroxyphenyl groups or have a lower alkyl group in both hydroxyphenyl groups.

The new 4,4'-dihydroxyphenyl bicyclohexenes proposed by the present invention are expressed by General Formula 1 below.

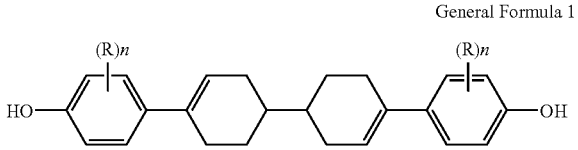

General Formula 1

(In the formula, R represents an alkyl group with a carbon atom number of 1 to 4, while n represents an integer of 0, or 1 to 3.)

In General Formula 1 above, R indicates an alkyl group with a carbon number of 1 to 4. Specifically, it is a methyl group, ethyl group, propyl group or butyl group. If R is given as a propyl group or butyl group, the propyl/butyl group may have a straight-chain or branched structure. n represents an integer of 0, or 1 to 3.

Specific examples of the 4,4'-dihydroxyphenyl bicyclohexenes proposed by the present invention, or 4,4'-dihydroxyphenyl bicyclohexenes-3, include 4,4'-di(4-hydroxyphenyl)bicyclohexene-3, 4,4'-di(2-methyl-4-hydroxyphenyl)bicyclohexene-3, 4,4'-di(3-methyl-4-hydroxyphenyl)bicyclohexene-3, 4,4'-di(3,5-dimethyl-4-hydroxyphenyl)bicyclohexene-3, 4,4'-di(3,6-dimethyl-4-hydroxyphenyl)bicyclohexene-3, 4,4'-di(2,3,5-trimethyl-4-hydroxyphenyl)bicyclohexene-3, 4,4'-di(2,3,6-trimethyl-4-hydroxyphenyl)bicyclohexene-3, 4,4'-di(3-ethyl-4-hydroxyphenyl)bicyclohexene-3, 4,4'-di(3-isopropyl-4-hydroxyphenyl)bicyclohexene-3, 4,4'-di(3-n propyl-4-hydroxyphenyl)bicyclohexene-3, 4,4'-di(3-n butyl-4-hydroxyphenyl)bicyclohexene-3, 4,4'-di(3-isobutyl-4-hydroxyphenyl)bicyclohexene-3 and 4,4'-di(3-t butyl-4-hydroxyphenyl)bicyclohexene-3.

These 4,4'-dihydroxyphenyl bicyclohexenes expressed by General Formula 1, as proposed by the present invention, can be obtained, for example, by thermally decomposing 4,4,4',4'-tetrahydroxyphenyl bicyclohexanes expressed by General Formula 2 below, preferably in the presence of alkali catalyst.

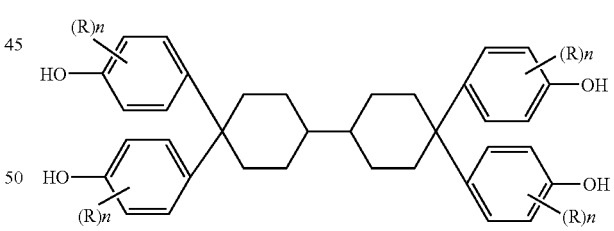

General Formula 2

(The definitions of R and n in the formula are the same as those of R and n in General Formula 1.)

Specific examples of the 4,4,4',4'-tetrahydroxyphenyl bicyclohexanes expressed by General Formula 2 above, which are used as the source material for producing the 4,4'-dihydroxyphenyl bicyclohexenes proposed by the present invention, include 4,4,4',4'-tetra(4-hydroxyphenyl)bicyclohexane, 4,4,4',4'-tetra(2-methyl-4-hydroxyphenyl)bicyclohexane, 4,4,4',4'-tetra(3-methyl-4-hydroxyphenyl)bicyclohexane, 4,4,4',4'-tetra(3,5-dimethyl-4-hydroxyphenyl)bicyclohexane, 4,4,4',4'-tetra(3,6-dimethyl-4-hydroxyphenyl)bicyclohexane, 4,4,4',4' tetra(2,3,5-trimethyl-4-hydroxyphenyl)bicyclohexane, 4,4,4',4'-tetra(2,3,6-trimethyl-4-hydroxyphenyl)bicyclohexane, 4,4,4',4'- tetra(3-ethyl-4-hydroxyphenyl)bicyclohexane, 4,4,4',4'-tetra (3-isopropyl-4-hydroxyphenyl)bicyclohexane, 4,4,4',4'-tetra (3-n propyl-4-hydroxyphenyl)bicyclohexane, 4,4,4',4'-tetra (3-isobutyl-4-hydroxyphenyl)bicyclohexane and 4,4,4',4'-tetra(3-t butyl-4-hydroxyphenyl)bicyclohexane.

The 4,4,4',4'-tetrahydroxyphenyl bicyclohexanes expressed by General Formula 2 above can be easily obtained, for example, by causing 4,4'-bicyclohexanon to react against substitutional phenols in the presence of acid catalyst, as described in Publication of Unexamined Patent Application No. 2000-34248.

It is possible to thermally decompose 4,4,4',4'-tetrahydroxyphenyl bicyclohexanes, expressed by General Formula 2 above, in the absence of catalyst. However, its thermal decomposition should preferably be conducted in the presence of alkali catalyst. The alkali catalyst used in this thermal decomposition is not limited to a specific type, but examples include sodium hydroxide, potassium hydroxide, lithium hydroxide or other alkali metal hydroxide; sodium carbonate, potassium carbonate or other alkali metal carbonate; sodium hydrogen carbonate, potassium hydrogen carbonate or other alkali metal hydrogen carbonate; sodium phenoxide, potassium phenoxide or other alkali metal phenoxide; and magnesium hydroxide, barium hydroxide or other alkaline-earth metal hydroxide. Among these, sodium hydroxide or potassium hydroxide is a preferred choice as the aforementioned alkali catalyst.

If alkali catalyst is used, the content of alkali catalyst should be normally 0.01 to 30 parts by weight, or preferably 0.1 to 15 parts by weight, with respect to 100 parts by weight of 4,4,4',4'-tetrahydroxyphenyl bicyclohexanes. Although the catalyst can be used in any form, it is preferable to provide it as an aqueous solution of 10 to 50 percent by weight, in order to facilitate its introduction into the reaction field.

The aforementioned thermal decomposition of 4,4,4',4'-tetrahydroxyphenyl bicyclohexanes should preferably be conducted in the presence of reaction solvent, partly because 4,4,4',4'-tetrahydroxyphenyl bicyclohexanes, or the source material, and/or 4,4'-dihydroxyphenyl bicyclohexanes, or the target product, have a high melting point and therefore their liquid property should be improved at the thermal decomposition temperature, and partly because thermal polymerization of the obtained target product should be prevented.

Any solvent can be used as the aforementioned reaction solvent, as long as it is inactive at the thermal decomposition temperature and is not distilled from the reaction mixture. Specific examples of the reaction solvent include triethylene glycol, tetraethylene glycol, pentaethylene glycol or other polyethylene glycol; and tripropylene glycol, tetrapropylene glycol, glycerin or other polyhydric alcohol.

In addition, commercially available organic heating media such as "Therm S" (manufactured by Nippon Steel Chemical Group) or "SK-OIL" (manufactured by Soken Chemical & Engineering Co., Ltd.) can also be used.

The content of this solvent should be normally 20 to 2,000 parts by weight, or preferably 100 to 800 parts by weight, with respect to 100 parts by weight of hydroxyphenyl-substituted cyclohexylidene bisphenol used.

The thermal decomposition of 4,4,4',4'-tetrahydroxyphenyl bicyclohexanes should be conducted normally in a temperature range of 150 to 300° C., or preferably in a temperature range of 180 to 250° C.

This is because if the thermal decomposition temperature is too low, it will take too long to achieve the reaction temperature. On the other hand, if the thermal decomposition temperature is too high, unwanted side reactions will increase. The reaction pressure during thermal decomposition is not limited to a specific level, but it should be usually in a range of normal pressure to vacuum pressure, such as 1 to 760 mmHg, or preferably 10 to 50 mmHg, by gauge pressure.

In the reaction conditions specified above, thermal decomposition of 4,4,4',4'-tetrahydroxyphenyl bicyclohexanes should normally complete in around one to six hours. The thermal decomposition reaction is deemed complete when alkyl phenols produced by the decomposition reaction are no longer distilled.

For example, a preferred mode of thermal decomposition is one in which hydroxyphenyl-substituted cyclohexylidene bisphenols and a solvent such as tetraethylene glycol are introduced to a reaction container, after which the container is heated to a temperature of 190 to 220° C. at a gauge pressure of 10 to 50 mmHg for around three to six hours while stirring the reaction mixture and distilling alkyl phenols produced by the decomposition reaction. By thermally decomposing the 4,4,4',4'-tetrahydroxyphenyl bicyclohexanes this way, the 4,4'-hydroxyphenyl-substituted bicyclohexenes proposed by the present invention can be obtained normally at a reaction yield of 90 percent or so. The 4,4'-hydroxyphenyl-substituted bicyclohexenes, which are the target products of the present invention, are expected to offer utility as a material for liquid crystal polyester, polycarbonate, polyurethane or other synthetic resins or for photoresist used with display elements, semiconductors, etc. In addition, the 4,4'-hydroxyphenyl-substituted bicyclohexenes proposed by the present invention also offer utility as an intermediate in various useful chemicals. For example, by dehydrogenating the cyclohexene part of 4,4'-hydroxyphenyl-substituted bicyclohexenes, 4,4"-hydroxyphenyl-substituted biphenyls can be produced. Alternatively, by hydrogenating the cyclohexene part of 4,4'-hydroxyphenyl-substituted bicyclohexenes, 4,4"-hydroxyphenyl-substituted bicyclohexanes can be produced. The obtained compounds are also expected to be useful as a material for liquid crystal polyester, polycarbonate, polyurethane or other synthetic resins or for photoresist used with display elements, semiconductors, etc.

BEST MODE FOR CARRYING OUT THE INVENTION

The present invention is explained in details by using examples.

REFERENCE EXAMPLE 1

Synthesis of 4,4,4',4'-tetra(4-hydroxyphenyl)bicyclohexane (the compound expressed by Formula 3)

A reaction container (four-way flask with a capacity of 1 liter), to which 209.4 g of phenol, 2.4 g of dodecyl mercaptan and 18.9 g of methanol were introduced, was replaced by nitrogen. Next, a solution made of 24.2 g of 4,4'-bicyclohexanon and 24.2 g of phenol dissolved in 24.2 g of methanol was dripped into the container over three hours at 40° C. while introducing hydrogen chloride gas under stirring. After the drip was completed, the reaction mixture was reacted for another 17 hours under stirring at the same temperature.

After the reaction, 2.5 g of 75-percent aqueous phosphoric acid solution and 111.8 g of 16-percent aqueous sodium hydroxide solution were added to the reaction mixture to neutralize the mixture to pH6. Then, a mixture made of 92.7 g of ethyl isobutyl ketone and 75.1 g of water was added to the neutralized solution at a heated temperature, after which the neutralized solution was cooled to cause crystallization, filtered, and then dried to obtain 63.3 g of 4,4,4',4'-tetra(4-hydroxyphenyl)bicyclohexane with a purity of 91.3 percent (by high-speed liquid chromatography) as light reddish white solid.

The yield with respect to the material 4,4'-bicyclohexanon was 89.6 mol percent.

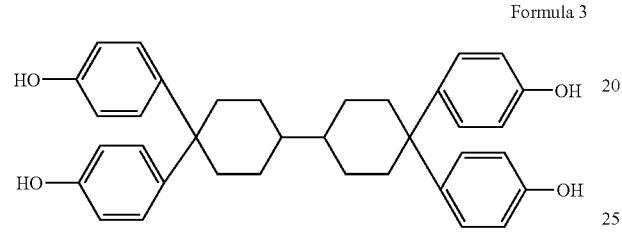

Formula 3

EXAMPLE 1

Synthesis of 4,4'-di(4-hydroxyphenyl)bicyclohexene-3 (the compound expressed by Formula 4)

A reaction container (four-way flask with a capacity of 1 liter), to which 63.3 g (0.112 mol) of the 4,4,4',4'-tetra(4-hydroxyphenyl)bicyclohexane (purity: 91.3 percent) obtained in Reference Example 1 above and 212 g of tetraethylene glycol were introduced, was replaced by nitrogen, after which 3.9 g (0.0468 mol) of 48-percent aqueous sodium hydroxide solution was added and the internal pressure of the reaction container was reduced to approx. 3.0 kPa to cause thermal decomposition reaction for three hours at 203° C.

The thermal decomposition reaction was deemed complete when distillate was no longer generated. After the reaction, 41.8 g of DI water and 50-percent aqueous acetic acid solution were added to neutralize the reaction mixture to approx. pH6, to obtain a slurry.

The obtained slurry was mixed with 83 g of methanol, crystallized, and then filtered to obtain 37.3 g of light yellow solid. Next, the obtained 37.3 g of light yellow solid and 149.4 g of water were introduced to a four-way flask with a capacity of 300 ml, after which the mixture was replaced by nitrogen and then stirred for two hours at 82° C. Thereafter, the slurry was cooled, filtered and dried to obtain 29.9 g of 4,4'-di(4-hydroxyphenyl)bicyclohexene-3 with a purity of 97.4 percent (by high-speed liquid chromatography) as light yellow powder.

The yield with respect to the material 4,4,4',4'-tetra(4-hydroxyphenyl)bicyclohexane was 73.4 mol percent.

Melting point: 318° C. (by differential thermal analysis)

Molecular weight: 347 (M+H)$^+$ (by mass spectrometry)

Proton NMR analysis (400 MHz, solvent: DMSO-d)

Formula 4

| Assignment | δ (ppm) | Signal | Proton number |
|---|---|---|---|
| a~h | 1.29~1.43<br>1.94~1.96<br>2.21~2.44 | m | 14 |
| I · j | 5.99 | s | 2 |
| k~r | 6.69, 7.22 | d | 8 |
| s · t | 9.31 | s | 2 |

REFERENCE EXAMPLE 2

Synthesis of 4,4,4'4'-tetra(3-methyl-4-hydroxyphenyl)bicyclohexane (the compound expressed by Formula 5)

The same method as specified in Reference Example 1 was used, except that 177.6 g of 0-cresol and 23.5 g of methanol were used instead of 209.4 g of phenol and 18.9 g of methanol, and that a solution made of 38.9 g of 4,4'-bicyclohexanon and 38.9 g of 0-cresol dissolved in 15.7 g of methanol was used instead of a solution made of 24.2 g of 4,4'-bicyclohexanon and 24.2 g of phenol dissolved in 24.2 g of methanol, to achieve reaction, neutralization, crystallization and filtering to obtain 235.5 g of 4,4,4'4'-tetra(3-methyl-4-hydroxyphenyl)bicyclohexane as white solid (still wet with the solution).

The yield with respect to the material 4,4'-bicyclohexanon was 86.5 mol percent.

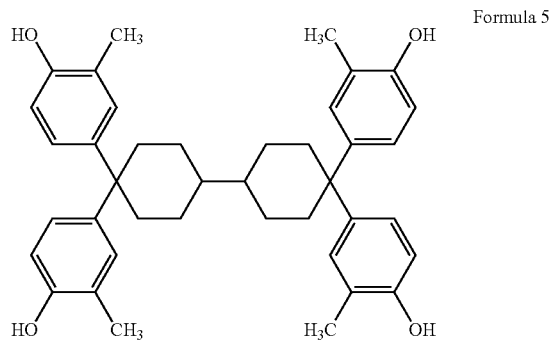

Formula 5

EXAMPLE 2

Synthesis of 4,4'-di(3-methyl-4-hydroxyphenyl) bicyclohexene-3 (the compound expressed by Formula 6):

A reaction container (four-way flask with a capacity of 1 liter, to which 235.5 g of the 4,4,4',4'-tetra(3-methyl-4-hydroxyphenyl)bicyclohexane obtained in Reference Example 2 above, 256.9 g of tetraethylene glycol and 2.7 g of 48-percent aqueous sodium hydroxide solution were introduced, was replaced by nitrogen, after which the internal pressure of the reaction container was reduced to approx. 3 kPa to cause thermal decomposition reaction for two and a half hours at 198° C.

After the reaction, 128 g of DI water and 50-percent aqueous acetic acid solution were added to neutralize the reaction mixture to approx. pH6, to obtain a slurry.

The obtained slurry was mixed with 202 g of methanol, crystallized, and then filtered to obtain 69.4 g of light reddish yellow solid.

Next, the obtained 69.4 g of light reddish yellow solid and 277 g of water were introduced to a four-way flask with a capacity of 500 ml, after which the mixture was processed in the same manner as in Example 1 to obtain 51.5 g of 4,4'-di(3-methyl-4-hydroxyphenyl)bicyclohexene-3 with a purity of 98.0 percent (by high-speed liquid chromatography) as light yellowish gray solid.

The yield with respect to the material 4,4,4',4'-tetra(3-methyl-4-hydroxyphenyl)bicyclohexane was 77.2 mol percent (the yield with respect to the material 4,4'-bicyclohexanon was 66.8 mol percent).

Melting point: 227° C. (by differential thermal analysis)
Molecular weight: 375 (M+H)$^+$ (by mass spectrometry)
Proton NMR analysis (400 MHz, solvent: DMSO-d)

Formula 6

| Assignment | δ (ppm) | Signal | Proton number |
|---|---|---|---|
| a, b | 2.20 | s | 6 |
| c~j | 1.38~1.49<br>2.02~2.12<br>2.27~2.52 | m | 14 |
| k~l | 6.01 | s | 2 |
| m~r | 6.74~6.76<br>7.06~7.09<br>7.17 | d<br>d<br>s | 6 |
| s, t | 8.07 | s | 2 |

REFERENCE EXAMPLE 3

Synthesis of 4,4,4'4'-tetra(3-isopropyl-4-hydroxyphenyl)bicyclohexane (the compound expressed by Formula 7)

The same method as specified in Reference Example 1 was used, except that 236.8 g of 0-isopropyl phenol and 23.7 g of methanol were used instead of 209.4 g of phenol and 18.9 g of methanol, and that a solution made of 39.0 g of 4,4'-bicyclohexanon and 39.0 g of 0-isopropyl phenol dissolved in 15.8 g of methanol was used instead of a solution made of 24.2 g of 4,4'-bicyclohexanon and 24.2 g of phenol dissolved in 24.2 g of methanol, to achieve reaction, neutralization, crystallization and filtering to obtain 175.9 g of 4,4,4'4'-tetra(3-isopropyl-4-hydroxyphenyl)bicyclohexene as white solid (still wet with the solution).

The yield with respect to the material 4,4'-bicyclohexanon was 78.7 mol percent.

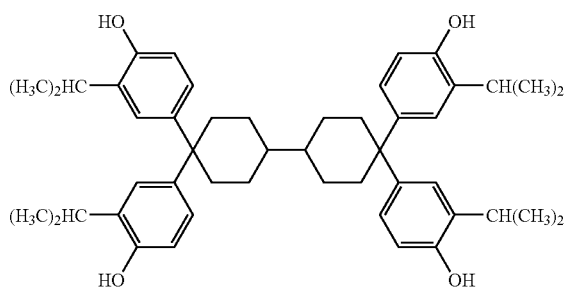

Formula 7

EXAMPLE 3

Synthesis of 4,4'-di(3-isopropyl-4-hydroxyphenyl)bicyclohexene-3 (the compound expressed by Formula 8)

A reaction container (four-way flask with a capacity of 1 liter), to which 175.9 g of the 4,4,4',4'-tetra(3-isopropyl-4-hydroxyphenyl)bicyclohexane obtained in Reference Example 3 above, 175.9 g of tetraethylene glycol and 2.9 g of 48-percent aqueous sodium hydroxide solution were introduced, was replaced by nitrogen, after which the internal pressure of the reaction container was reduced to approx. 3 kPa to cause thermal decomposition reaction for three hours and forty minutes at 198° C.

After the reaction, 140 g of DI water and 50-percent aqueous acetic acid solution were added to neutralize the reaction mixture to approx. pH6, to obtain a slurry.

The obtained slurry was mixed with 141 g of toluene, heated to 60° C. to dissolve the crystal, and then flushed with water. Then, the water phase was separated and an oil phase containing the target product was obtained. Next, the obtained oil phase was mixed with methyl isobutyl ketone and water and washed, after which the water phase was separated and an oil phase was obtained again. The obtained oil phase was cooled and the precipitated crystal was filtered and then dried to obtain 39.2 g of light yellow solid with a purity of 98.3 percent (by high-speed liquid chromatography).

The yield with respect to the material 4,4,4',4'-tetra(3-isopropyl-4-hydroxyphenyl)bicyclohexane was 56.7 mol percent (the yield with respect to the material 4,4'-bicyclohexanon was 44.6 mol percent).

Melting point: 165° C. (by differential thermal analysis)
Molecular weight: 431 (M+H)$^+$ (by mass spectrometry)
Proton NMR analysis (400 MHz, solvent: DMSO-d)

Formula 8

| Assignment | δ (ppm) | Signal | Proton number |
|---|---|---|---|
| a~d | 1.26~1.31 | d | 12 |
| e~l | 1.36~1.53 | m | 14 |

-continued

Formula 8

| Assignment | δ (ppm) | Signal | Proton number |
|---|---|---|---|
| | 2.00~2.03 | | |
| | 2.27~2.52 | | |
| m, n | 3.14~3.25 | m | 2 |
| o, p | 4.65 | s | 2 |
| q, r | 6.03 | s | 2 |
| s~x | 6.68~6.70 | d | 6 |
| | 7.06~7.11 | d | |
| | 7.22~7.25 | s | |

REFERENCE EXAMPLE 4

Synthesis of 4,4,4'4'-tetra(3,5-dimethyl-4-hydroxyphenyl)bicyclohexane (the compound expressed by Formula 9)

The same method as specified in Reference Example 1 was used, except that 352.6 g of 2,6-xylenol and 35.3 g of methanol were used instead of 209.4 g of phenol and 18.9 g of methanol, and that a solution made of 66.7 g of 4,4'-bicyclohexanon and 66.7 g of 2,6-xylenol dissolved in 31.4 g of methanol was used instead of a solution made of 24.2 g of 4,4'-bicyclohexanon and 24.2 g of phenol dissolved in 24.2 g of methanol, to achieve reaction, neutralization, crystallization and filtering to obtain 295.1 g of 4,4,4'4'-tetra(3,5-dimethyl-4-hydroxyphenyl)bicyclohexane as white solid (still wet with the solution).

The yield with respect to the material 4,4'-bicyclohexanon was 95.1 mol percent.

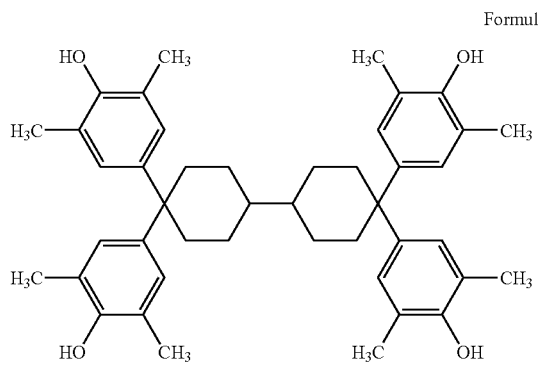

Formula 9

EXAMPLE 4

Synthesis of 4,4'-di(3,5-dimethyl-4-hydroxyphenyl)bicyclohexene-3 (the compound expressed by Formula 10)

A reaction container (four-way flask with a capacity of 2 liters), to which 295.1 g of the 4,4,4'4'-tetra(3,5-dimethyl-4-hydroxyphenyl)bicyclohexane obtained in Reference Example 4 above, 401.5 g of tetraethylene glycol and 5.0 g of 48-percent aqueous sodium hydroxide solution were introduced, was replaced by nitrogen, after which the internal pressure of the reaction container was reduced to approx. 3 kPa to cause thermal decomposition reaction for two and a half hours at 199° C.

After the reaction, 200 g of DI water and 50-percent aqueous acetic acid solution were added to neutralize the reaction mixture to approx. pH6, to obtain a slurry.

The obtained slurry was mixed with 332 g of methanol, crystallized, and then filtered to obtain 131.2 g of yellow solid.

Next, the obtained 131.2 g of yellow solid and 524 g of water were introduced to a four-way flask with a capacity of 1,000 ml, and the mixture was processed in the same manner as in Example 1 to obtain 112.3 g of 4,4'-di(3,5-dimethyl-4-hydroxyphenyl)bicyclohexene-3 with a purity of 98.9 percent (by high-speed liquid chromatography) as yellow solid.

The yield with respect to the material 4,4,4',4'-tetra(3-isopropyl-4-hydroxyphenyl)bicyclohexane was 84.5 mol percent (the yield with respect to the material 4,4'-bicyclohexanon was 80.4 mol percent).

Melting point: 233° C. (by differential thermal analysis)

Molecular weight: 403 (M+H)$^+$ (by mass spectrometry)

Proton NMR analysis (400 MHz, solvent: DMSO-d)

Formula 10

| Assignment | δ (ppm) | Signal | Proton number |
|---|---|---|---|
| a~d | 2.12 | s | 12 |
| e~l | 1.27~1.39 | m | 14 |
| | 1.94~1.98 | | |
| | 2.14~2.43 | | |
| m, n | 5.95 | s | 2 |
| o~r | 6.94 | s | 4 |
| s, t | 8.10 | s | 2 |

INDUSTRIAL FIELD OF APPLICATION

The new 4,4'-hydroxy phenyl-substituted bicyclohexenes proposed by the present invention have no substitutional group in either of the hydroxyphenyl groups or have a lower alkyl group in both hydroxyphenyl groups, and are expected to offer improved performance compared with 1,4-hydroxyphenyl-substituted cyclohexene compounds having the cyclohexene structure in terms of melting point, heat resistance and weather resistance, among others. Also, the 4,4'-hydroxyphenyl-substituted bicyclohexenes themselves are useful as a material for liquid crystal polyester, polycarbonate, polyurethane or other synthetic resins or for photoresist used with display elements, semiconductors, etc. They are also useful as an intermediate in various useful compounds.

The invention claimed is:

1. 4,4'-dihydroxyphenyl bicyclohexenes expressed by General Formula 1 below (in the formula, R represents an alkyl group with a carbon atom number of 1 to 4, while n represents an integer of 0, or 1 to 3):

General Formula 1

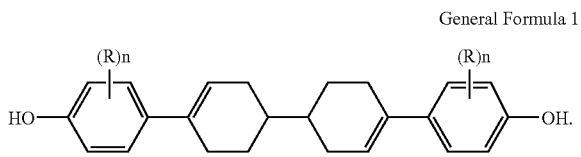

2. The 4,4'-dihydroxyphenyl bicyclohexenes of claim 1, wherein R is selected from the group consisting of methyl group, ethyl group, propyl group, and butyl group.

3. The 4,4'-dihydroxyphenyl bicyclohexenes of claim 1, which is 4,4'-di(4-hydroxyphenyl)bicyclohexene-3.

4. The 4,4'-dihydroxyphenyl bicyclohexenes of claim 1, which is 4,4'-di(2-methyl-4-hydroxyphenyl)bicyclohexene-3.

5. The 4,4'-dihydroxyphenyl bicyclohexenes of claim 1, which is 4,4'-di(3-methyl-4-hydroxyphenyl)bicyclohexene-3.

6. The 4,4'-dihydroxyphenyl bicyclohexenes of claim 1, which is 4,4'-di(3,5-dimethyl-4-hydroxyphenyl)bicyclohexene-3.

7. The 4,4'-dihydroxyphenyl bicyclohexenes of claim 1, which is 4,4'-di(3,6-dimethyl-4-hydroxyphenyl)bicyclohexene-3.

8. The 4,4'-dihydroxyphenyl bicyclohexenes of claim 1, which is 4,4'-di(2,3,5-trimethyl-4-hydroxyphenyl)bicyclohexene-3.

9. The 4,4'-dihydroxyphenyl bicyclohexenes of claim 1, which is 4,4'-di(2,3,6-trimethyl-4-hydroxyphenyl)bicyclohexene-3.

10. The 4,4'-dihydroxyphenyl bicyclohexenes of claim 1, which is 4,4'-di(3-ethyl-4-hydroxyphenyl)bicyclohexene-3.

11. The 4,4'-dihydroxyphenyl bicyclohexenes of claim 1, which is 4,4'-di(3-isopropyl-4-hydroxyphenyl)bicyclohexene-3.

12. The 4,4'-dihydroxyphenyl bicyclohexenes of claim 1, which is 4,4'-di(3-n propyl-4-hydroxyphenyl)bicyclohexene-3.

13. The 4,4'-dihydroxyphenyl bicyclohexenes of claim 1, which is 4,4'-di(3-n butyl-4-hydroxyphenyl)bicyclohexene-3.

14. The 4,4'-dihydroxyphenyl bicyclohexenes of claim 1, which is 4,4'-di(3-isobutyl-4-hydroxyphenyl)bicyclohexene-3.

15. The 4,4'-dihydroxyphenyl bicyclohexenes of claim 1, which is 4,4'-di(3-t butyl-4-hydroxyphenyl)bicyclohexene-3.

16. A method of producing the 4,4'-dihydroxyphenyl bicyclohexenes of claim 1, comprising thermally decompose 4,4,4',4'-tetrahydroxyphenyl bicyclohexanes, expressed by General Formula 2 below:

General Formula 2

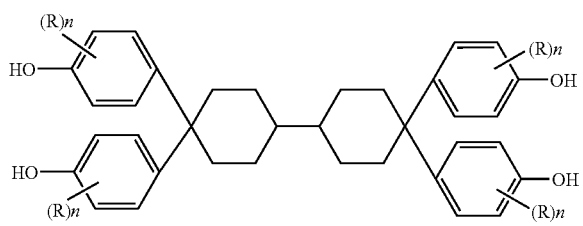

wherein the definitions of R and n in the formula are the same as those of R and n in General Formula 1.

17. The method according to claim 16, wherein the thermal decomposition is conducted in the presence of alkali catalyst.

18. The method according to claim 17, wherein the alkali catalyst is selected from the group consisting of sodium hydroxide, potassium hydroxide, lithium hydroxide or other alkali metal hydroxide; sodium carbonate, potassium carbonate or other alkali metal carbonate; sodium hydrogen carbonate, potassium hydrogen carbonate or other alkali metal hydrogen carbonate; sodium phenoxide, potassium phenoxide or other alkali metal phenoxide; and magnesium hydroxide, barium hydroxide, and other alkaline-earth metal hydroxide.

19. The method according to claim 16, wherein the thermal decomposition is conducted in the presence of reaction solvent.

20. The method according to claim 16, wherein the thermal decomposition is conducted at a temperature of 150–300° C.

* * * * *